US009492294B2

(12) United States Patent
Pacetti

(10) Patent No.: US 9,492,294 B2
(45) Date of Patent: *Nov. 15, 2016

(54) IMPLANTABLE PROSTHESIS HAVING THROUGH-HOLES

(71) Applicant: Abbott Cardiovascular Systems Inc., Santa Clara, CA (US)

(72) Inventor: Stephen D. Pacetti, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/034,953

(22) Filed: Sep. 24, 2013

(65) Prior Publication Data

US 2014/0025160 A1    Jan. 23, 2014

Related U.S. Application Data

(63) Continuation of application No. 12/752,761, filed on Apr. 1, 2010, now Pat. No. 8,551,159.

(51) Int. Cl.
*A61F 2/91* (2013.01)
*A61F 2/90* (2013.01)
*A61F 2/915* (2013.01)

(52) U.S. Cl.
CPC ............. *A61F 2/90* (2013.01); *A61F 2/915* (2013.01); *A61F 2002/91575* (2013.01); *A61F 2210/0004* (2013.01); *A61F 2230/0054* (2013.01); *A61F 2240/001* (2013.01); *A61F 2250/0068* (2013.01)

(58) Field of Classification Search
CPC .................................. A61F 2/82; A61F 2/06
USPC ................................................. 623/1.15–1.48
See application file for complete search history.

(56) References Cited

U.S. PATENT DOCUMENTS 8,551,159 B2*  10/2013  Pacetti ........................ 623/1.42
8,562,670 B2*  10/2013  Pacetti et al. ................ 623/1.42
2009/0076591 A1*  3/2009  Girton et al. ................ 623/1.16

FOREIGN PATENT DOCUMENTS

WO    WO 2009/094270    7/2009

OTHER PUBLICATIONS

Japan Patent Office, Notice of Reasons for Rejection dispatched Oct. 21, 2014 for Patent Application No. P2013-502654, English translation, 6 pages.
Japan Patent Office, Final Rejection dispatched Aug. 4, 2015 for Patent Application No. P2013-502654, English translation, 5 pages.

* cited by examiner

*Primary Examiner* — Suzette J Gherbi
(74) *Attorney, Agent, or Firm* — Squire Patton Boggs (US) LLP

(57) ABSTRACT

A prosthesis for intraluminal drug delivery can comprise a plurality of interconnected struts and links that form a tubular structure. The struts and links can have luminal surfaces facing radially inward, abluminal surfaces facing radially outward, and side surfaces connecting the luminal surfaces to the abluminal surfaces. At least some of the struts and links have through-holes in the side surfaces. At least some of the through-holes contain a drug, which can be carried in a polymer matrix.

18 Claims, 10 Drawing Sheets

IMPLANTABLE PROSTHESIS HAVING THROUGH-HOLES

CROSS-REFERENCE TO RELATED APPLICATION

This application is a continuation of application Ser. No. 12/752,761, filed Apr. 1, 2010, now U.S. Pat. No. 8,551,159, which application is incorporated herein by reference.

FIELD OF THE INVENTION

Briefly and in general terms, the present invention generally relates to an implantable prosthesis and, more particularly, to a drug eluting stent.

BACKGROUND OF THE INVENTION

In percutaneous transluminal coronary angioplasty (PTCA), a balloon catheter is inserted through a brachial or femoral artery, positioned across a coronary artery occlusion, and inflated to compress against atherosclerotic plaque to open, by remodeling, the lumen of the coronary artery. The balloon is then deflated and withdrawn. Problems with PTCA include formation of intimal flaps or torn arterial linings, both of which can create another occlusion in the lumen of the coronary artery. Moreover, thrombosis and restenosis may occur several months after the procedure and create a need for additional angioplasty or a surgical bypass operation. Stents are used to address these issues. Stents are small, intricate, implantable medical devices and are generally left implanted within the patient to reduce occlusions, inhibit thrombosis and restenosis, and maintain patency within vascular lumens such as, for example, the lumen of a coronary artery.

The treatment of a diseased site or lesion with a stent involves both delivery and deployment of the stent. Stent delivery refers to introducing and transporting the stent through an anatomical lumen to a desired treatment site, such as a lesion in a vessel. An anatomical lumen can be any cavity, duct, or a tubular organ such as a blood vessel, urinary tract, and bile duct. Stent deployment corresponds to expansion of the stent within the anatomical lumen at the region requiring treatment. Delivery and deployment of a stent are accomplished by positioning the stent about one end of a catheter, inserting the end of the catheter through the skin into an anatomical lumen, advancing the catheter in the anatomical lumen to a desired treatment location, expanding the stent at the treatment location, and removing the catheter from the lumen with the stent remaining at the treatment location.

In the case of a balloon expandable stent, the stent is mounted about a balloon disposed on the catheter. Mounting the stent typically involves compressing or crimping the stent onto the balloon prior to insertion in an anatomical lumen. At the treatment site within the lumen, the stent is expanded by inflating the balloon. The balloon may then be deflated and the catheter withdrawn from the stent and the lumen, leaving the stent at the treatment site. In the case of a self-expanding stent, the stent may be secured to the catheter via a retractable sheath. When the stent is at the treatment site, the sheath may be withdrawn which allows the stent to self-expand.

Stents are often modified to provide drug delivery capabilities to further address thrombosis and restenosis. Stents may be coated with a polymeric carrier impregnated with a drug or therapeutic substance. A conventional method of coating includes applying a composition including a solvent, a polymer dissolved in the solvent, and a therapeutic substance dispersed in the blend to the stent by immersing the stent in the composition or by spraying the composition onto the stent. The solvent is allowed to evaporate, leaving on the stent strut surfaces a coating of the polymer and the therapeutic substance impregnated in the polymer.

The application of a uniform coating with good adhesion to a substrate can be difficult for small and intricate medical devices, such as certain stents for coronary and peripheral arteries. Such stents can be quite small. Stents for the coronary vessel anatomy typically have an overall diameter of only a few millimeters and a total length of several millimeters to tens of millimeters. Stents for the peripheral vessel anatomy are generally greater in diameter and length. Such peripheral stents may have a diameter up to 10 mm and a length of up to a few hundred millimeters. These stents may be constructed of a fine mesh network of struts, which provide support or push against the walls of the anatomical lumen in which the stent is implanted.

Conventional drug eluting stents have a drug coating that covers all surfaces of the stent strut, referred to as a conformal drug coating. With a conformal drug coating, the abluminal, luminal, and side surfaces of the strut release the drug. Abluminal surfaces face toward and contact the anatomical tissue, such as a blood vessel wall. Luminal surfaces face toward the center of the anatomical lumen and make contact with fluids in the anatomical lumen. Other drug eluting stents include depots or pockets with openings on the abluminal and/or luminal surfaces of the stent strut. With these types of drug eluting stents there are concerns with uniformity of the drug concentration generated within the patient. In general, drug concentration should be kept at a level that provides therapeutic effect and avoids or minimizes toxicity.

One study has shown that the drug concentration generated from conventional stents having a conformal drug coating varies significantly across the stent. For some stent strut patterns after a few days from implantation, drug concentration variability corresponding to plus and minus two standard deviations was found to be $3.3 \times 0^{-5} \pm 2.4 \times 10^{-5}$ kg/m$^3$. This gives a drug concentration range of $0.9 \times 10^{-5}$ to $5.7 \times 10^{-5}$ kg/m$^3$, which is about a factor of six. This very wide range can be acceptable for some drugs which have a wide therapeutic window (i.e., provide a therapeutic effect without toxicity over a wide concentration). However, this very wide range is of concern for drugs with relatively higher toxicity such as paclitaxel.

Accordingly, there is a continuing need for an implantable prosthesis and method of intraluminal drug delivery with improved drug concentration uniformity.

SUMMARY OF THE INVENTION

Briefly and in general terms, the present invention is directed to an implantable prosthesis. In aspects of the present invention, an implantable prosthesis comprises a plurality of interconnected struts and links that form a tubular structure. The struts and links have luminal surfaces facing radially inward, abluminal surfaces facing radially outward, and side surfaces connecting the luminal surfaces to the abluminal surfaces. At least some of the struts and links have through-holes in the side surfaces. In other aspects, the implantable prosthesis further comprises a therapeutic agent within the through-holes. In further aspects, the implantable prosthesis further comprises a coating on an external surface of the tubular structure, the coating carrying a therapeutic agent that is the same as or different from the therapeutic agent within the through-holes.

In some aspects of the present invention, an implantable prosthesis comprises a tubular frame of interconnected structural members, the structural members having non-radial through-holes, and a therapeutic agent within the non-radial through-holes. In other aspects, the implantable prosthesis further comprises a coating on an external surface of the structural members. The coating including a therapeutic agent that is the same as or different from the therapeutic agent within the non-radial through-holes. In further aspects, there is no therapeutic agent is disposed over any radially inward facing surface of the tubular frame, and no therapeutic agent is disposed over any radially outward facing surface of the tubular frame.

The features and advantages of the invention will be more readily understood from the following detailed description which should be read in conjunction with the accompanying drawings.

DETAILED DESCRIPTION OF THE PREFERRED EMBODIMENTS

Figure 1:
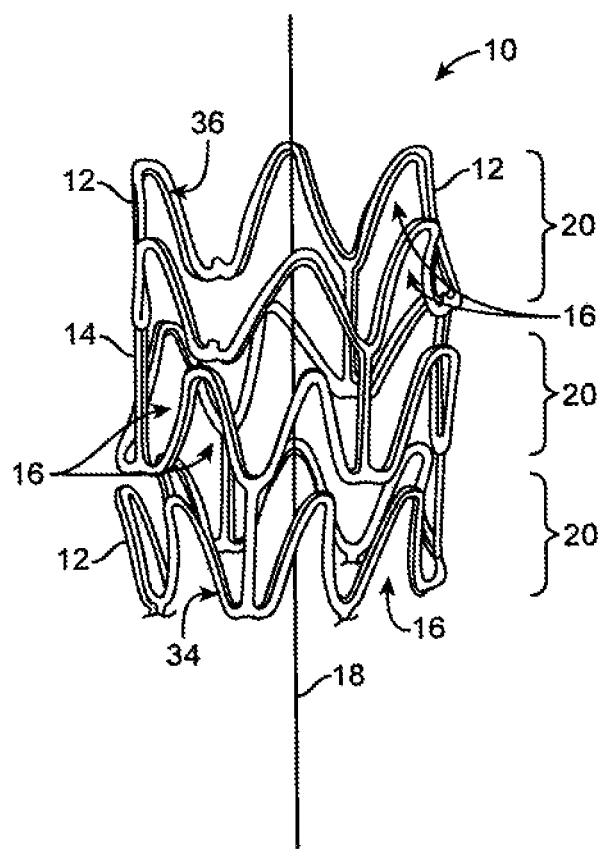
FIG. 1 is a is a perspective view of an end portion of a stent.

Referring now in more detail to the exemplary drawings for purposes of illustrating embodiments of the invention, wherein like reference numerals designate corresponding or like elements among the several views, there is shown in FIG. 1 an upper portion of a stent 10 having an overall body shape that is hollow and tubular. The stent can be balloon expandable or self-expandable.

The present invention encompasses stents having any particular geometrical configuration, such as a zig-zag, sinusoidal or serpentine strut configuration, and should not be limited to the patterns illustrated herein. The variation in stent patterns is virtually unlimited.

Figure 2:
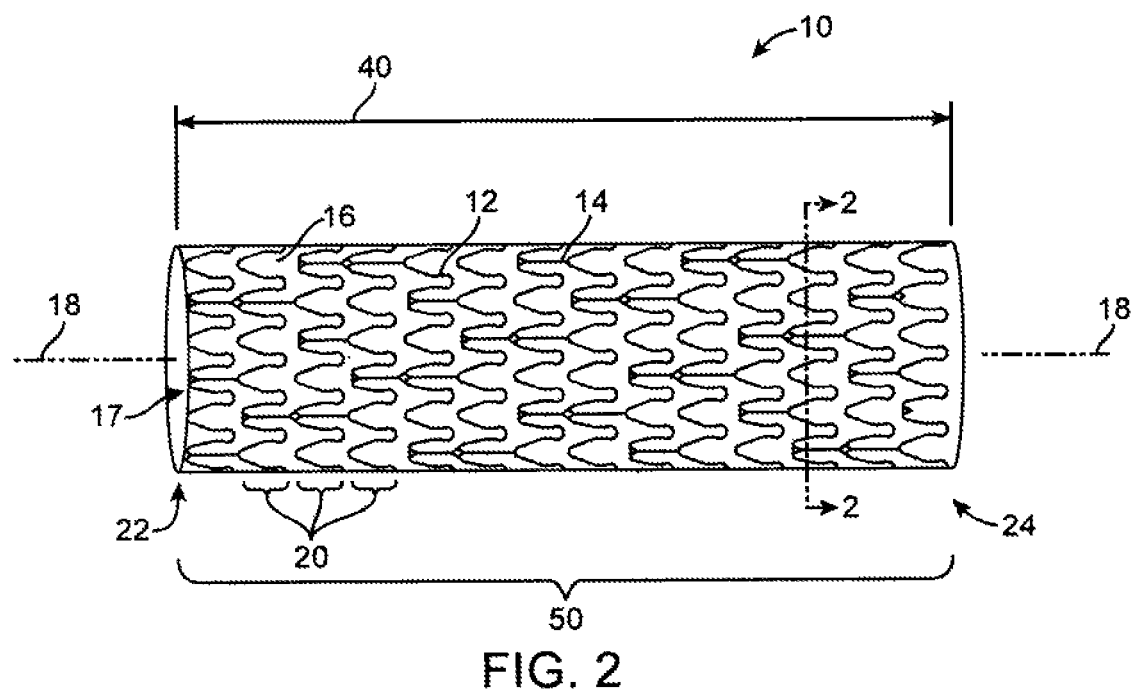
FIGS. 2 and 3 are perspective and radial cross-sectional views, respectively, of a stent.

FIGS. 1 and 2 show stents with two different stent patterns. The stents are illustrated in an uncrimped or expanded state. In both FIGS. 1 and 2 the stent 10 includes many interconnecting struts 12, 14 separated from each other by gaps 16. The struts 12, 14 form a tubular frame and can be made of any suitable material, such as a biocompatible metal or polymer. The material can be non-bioabsorable or bioabsorbable.

As used herein, the terms "bioabsorbable" and "biodegradable" are used interchangeably and refer to materials that are capable of being degraded or absorbed when exposed to bodily fluids such as blood, and components thereof such as enzymes, and that can be gradually resorbed, absorbed, and/or eliminated by the body.

The stent 10 has an overall longitudinal length 40 measured from opposite ends, referred to as the distal and proximal ends 22, 24. The stent 10 has an overall body 50 having a tube shape with a central passageway 17 passing through the entire longitudinal length of the stent. The central passageway has two circular openings, there being one circular opening at each of the distal and proximal ends 22, 24 of the overall tubular body 50. A central axis 18 runs through the central passageway in the center of the tubular frame or body 50. At least some of the struts 12 are arranged in series to form sinusoidal or serpentine ring structures 20 that encircle the central axis 18. The ring structures 20 are connected to each other by other struts 14, referred to as links, that are substantially straight and are oriented longitudinally. In some embodiments, the ring structures 20 are configured to be crimped and subsequently radially expanded.

Figure 3:
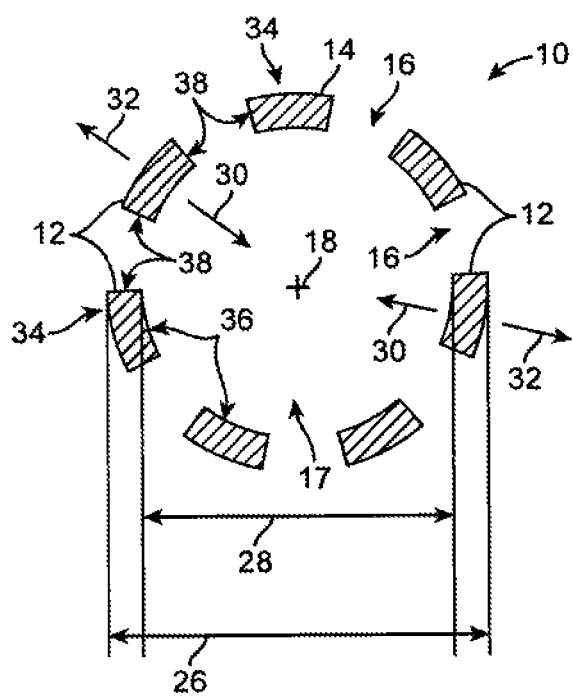

FIG. 3 is an exemplary radial cross-sectional view of the stent 10 along line 2-2 in FIG. 2. There can be any number of struts 12, 14 along line 2-2, which runs perpendicular to the central axis 18 of the stent 10. In FIG. 3, the cross-section of seven struts 12, 14 are shown for ease of illustration. The struts 12, 14 in cross-section are arranged in a circular pattern having an outer diameter 26 and an inner diameter 28. The circular pattern encircles the central axis

18. A portion of the surface of each strut faces radially inward in a direction 30 facing toward the central axis 18. A portion of the surface of each strut faces radially outward in a direction 32 facing away from the central axis 18. The various strut surfaces that face radially outward are individually referred to as abluminal surfaces 34. The abluminal surfaces of the struts collectively form the abluminal surface of the stent 10. The various strut surfaces that face radially inward are individually referred to as luminal surfaces 36. The luminal surfaces of the struts collectively form the luminal surface of the stent 10. Side surfaces 38 connect the luminal surfaces 36 to the abluminal surfaces 34. In the illustrated embodiment, the side surfaces 38 are flat and extend radially.

The terms "axial" and "longitudinal" are used interchangeably and relate to a direction, line or orientation that is parallel or substantially parallel to the central axis of a stent or a central axis of a cylindrical or tubular structure. The term "circumferential" relates to the direction along a circumference of a stent or a circular structure. The terms "radial" and "radially" relate to a direction, line or orientation that is perpendicular or substantially perpendicular to the central axis of a stent or a central axis of a cylindrical or tubular structure.

As shown for example in FIGS. 4-9, at least some of the struts have through-holes 50 (50T, 50A, 50R). The through-holes 50 are different from the gaps 16 (FIGS. 2 and 3) in that the through-holes 50 are formed into individual struts 12, 14, whereas the gaps 16 are disposed between two of more of the struts 12, 14. Also, the gaps 16 change in size as a result of crimping and radial expansion of the stent structure whereas the through-holes 50 do not change in size as a result of crimping and radial expansion. Further, the through-holes 50 have a cross-dimension or diameter that is no greater than the cross-dimension or width of an individual strut, whereas the gaps 16 have a cross-dimension that often exceeds that of the struts.

The term "through-hole" refers to a passageway that extends entirely through a structure and has openings at opposite ends of the passageway. Through-holes can be straight with no bend, as shown in FIGS. 4-9, or they can be slightly curved or bent. Through-holes are different from blind-holes and grooves which have only a single opening and do not extend entirely through a structure. Each of the through-holes have exactly two end openings.

In some embodiments, the openings at opposite ends of the through-holes 50 have a diameter from 10 um to 250 um, and more narrowly from 40 um to 100 um. In some embodiments, the through-holes have an average diameter across the entire end-to-end length of the through-holes from 10 um to 250 um, and more narrowly from 40 um to 100 um.

Figure 4:
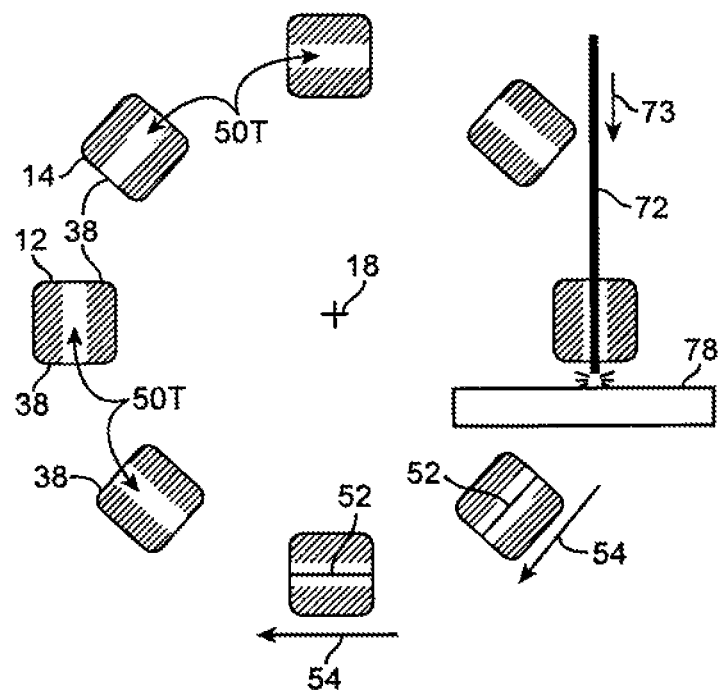
FIG. 4 is a radial cross-sectional view of a stent, showing stent struts with transverse through-holes for carrying a therapeutic agent to be delivered intraluminally.

In some embodiments, as shown in FIG. 4, through-holes 50T are oriented transversely or extend transversely through the struts 12, 14. Each of the transverse through-holes 50T has an end-to-end length 52 that extends in a transverse direction 54. The phrase "transverse direction" refers to a direction that runs substantially at a tangent to a circle around the central axis 18 and which does not intersect the central axis 18. The term "end-to-end length" refers to a straight line segment that starts from the center of one through-hole opening, ends at the center of the opposite through-hole opening, and runs through the through-hole passageway without intersecting walls of the through-hole. As shown in FIG. 4, the transverse through-holes 50 pass through side surfaces 38 that face in opposite directions. In other embodiments, all or only some of the through-holes in an implantable prosthesis are oriented transversely.

Figure 5:
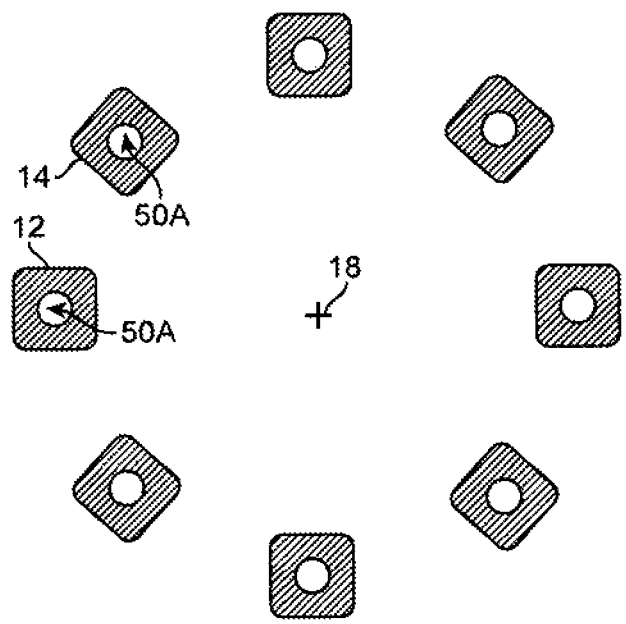
FIG. 5 is a radial cross-sectional view of a stent, showing stent struts with axial through-holes for carrying a therapeutic agent.
Figure 11:
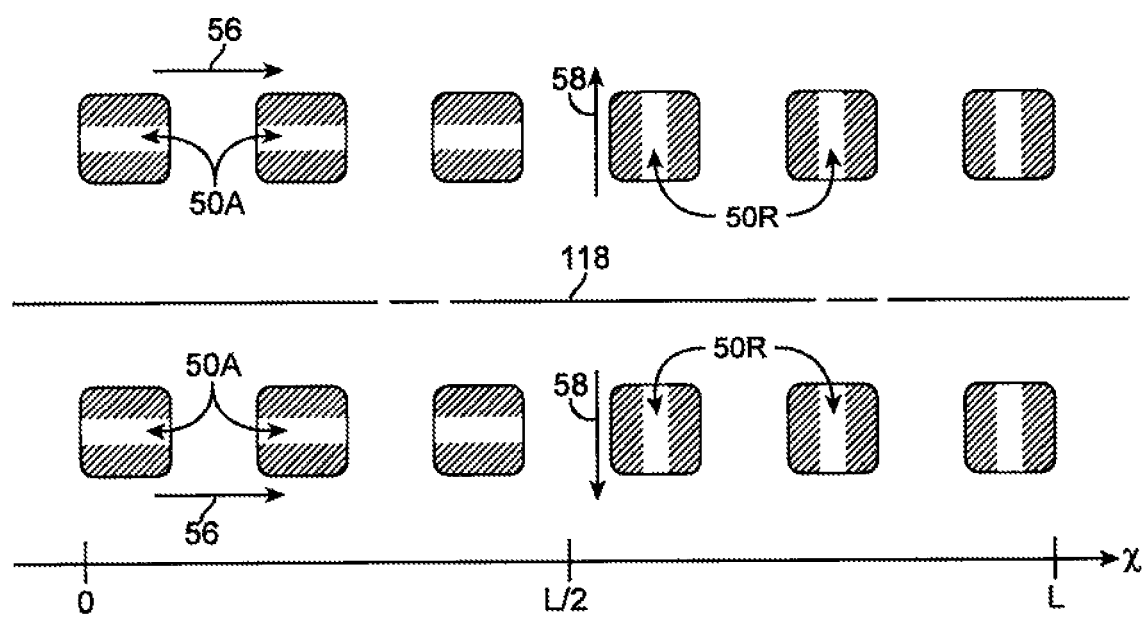
FIG. 11 is a longitudinal cross-sectional view of a stent having a longitudinal, stepped gradient in the ratio of the number of non-radial through-holes to the total number of through-holes.

In some embodiments, as shown in FIGS. 5 and 11, through-holes 50 are oriented axially or extend axially through the struts. Each of the axial through-holes 50A has an end-to-end length that extends in an axial direction 56 (see FIG. 11) that is substantially parallel to the central axis 18. The axial through-holes pass through side surfaces 38 that face in opposite axial directions. In other embodiments, all or only some of the through-holes in an implantable prosthesis are oriented axially.

Figure 6:
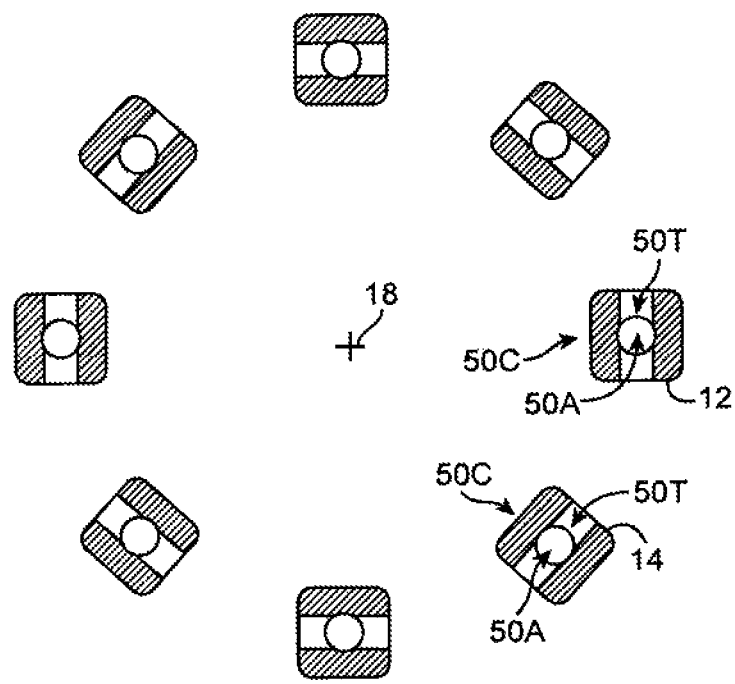
FIG. 6 is a radial cross-sectional view of a stent, showing stent struts with cross-holes for carrying a therapeutic agent, each of the cross-holes formed by a transverse through-hole and an axial through-hole.

In some embodiments, as shown in FIG. 6, a stent has transverse through-holes 50T and axial through-holes 50A. A cross-hole 50C in a strut 12, 14 is formed by at least two intersecting through-holes. Each transverse through-hole 50T and axial through-hole 50A has a diameter that is substantially uniform throughout its entire end-to-end length except at the area of the intersection. The intersecting through-holes intersect each other at or about the midpoint of their respective end-to-end lengths. As compared to a single through-hole, cross-holes can have a greater internal volume available for carrying a drug. In FIG. 6, each one of the transverse through-holes 50T is intersected by one of the axial through-holes 50A, and vice-versa. In other embodiments, all or only some of the transverse and axial through-holes of an implantable prosthesis are intersected by another through-hole.

Figure 7:
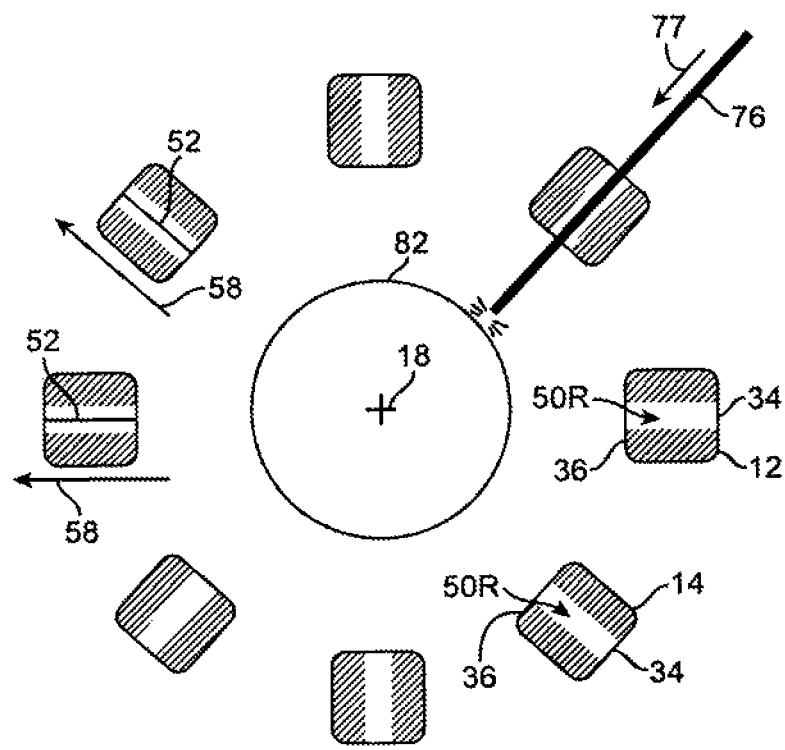
FIG. 7 is a radial cross-sectional view of a stent, showing stent struts with radial through-holes for carrying a therapeutic agent.

In some embodiments, as shown in FIG. 7, through-holes 50 are oriented radially or extend radially through struts 12, 14. Each of the radial through-holes 50R has an end-to-end length 52 that extends in a radial direction 58 away from the central axis 18. The radial through-holes pass through the abluminal surfaces 34 and luminal surfaces 36 of the struts 12, 14. In other embodiments, all or only some of the through-holes in an implantable prosthesis are oriented radially.

Figure 8:
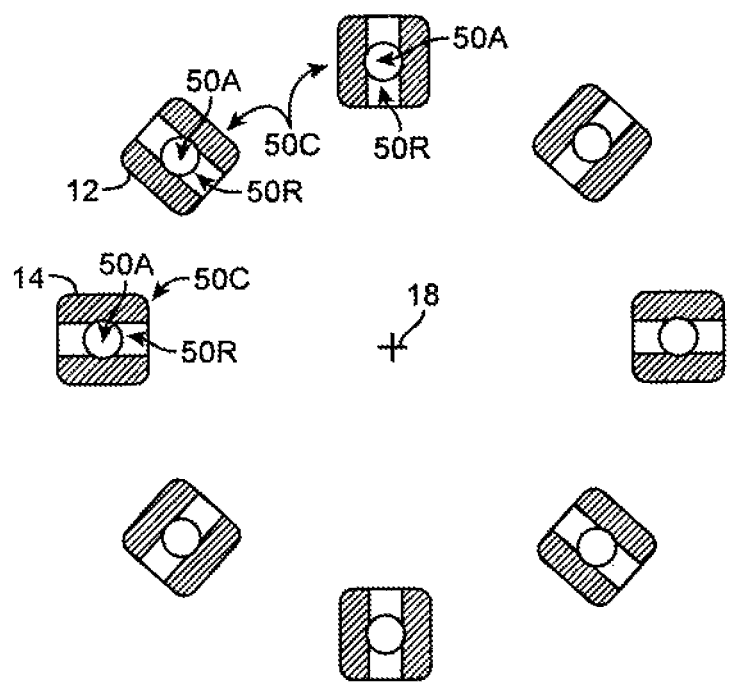
FIG. 8 is a radial cross-sectional view of a stent, showing stent struts with cross-holes for carrying a therapeutic agent, each of the cross-holes formed by an axial through-hole and a radial through-hole.

In some embodiments, as shown in FIG. 8, a stent has axial through-holes 50A and radial through-holes 50R. Each one of the axial through-holes 50A is intersected by one of the radial through-holes 50R, and vice-versa. In other embodiments, all or only some of the axial and radial through-holes of an implantable prosthesis is intersected by another through-hole.

Figure 9:
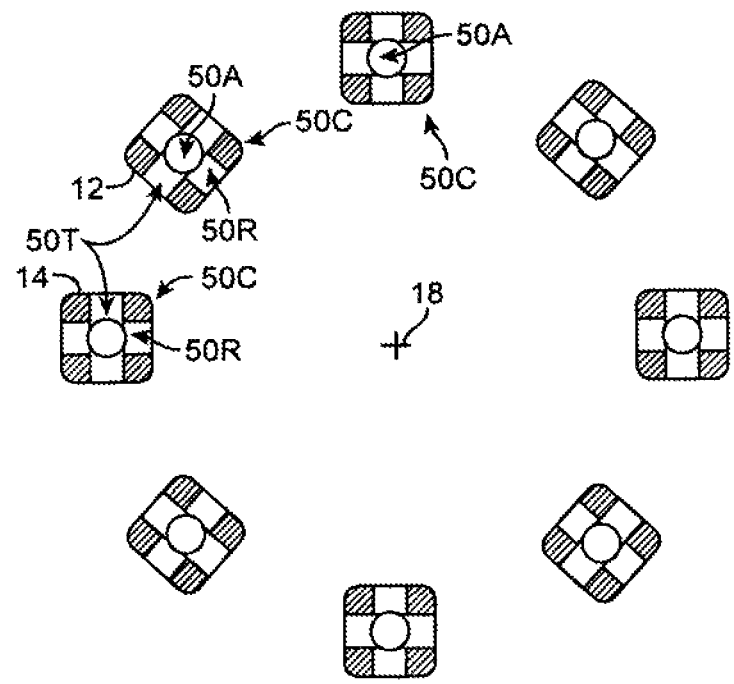
FIG. 9 is a radial cross-sectional view of a stent, showing stent struts with cross-holes for carrying a therapeutic agent, each of the cross-holes formed by mutually intersecting axial, radial, and transverse through-holes.

In some embodiments, as shown in FIG. 9, a stent has transverse through-holes 50T, axial through-holes 50A, and radial through-holes 50R which intersect each other at or about the center of their respective end-to-end lengths. In this way, a drug located in the mutually intersecting through-holes is located at every abluminal, luminal, and side surface of the struts. Upon deployment in a patient, the drug can be released from all sides of a strut 12, 14 to provide a drug distribution similar to conformally coated stents. When used as an alternative to or in combination with a conformal drug coating, the three-way cross holes 50C can allow the stent to release the drug over a longer period of time. In FIG. 9, each one of the transverse through-holes 50T is intersected by one of the axial through-holes 50A and by one of the radial through-holes 50R. In other embodiments, all or only some of the transverse through-holes 50T, axial through-holes 50A, and radial through-holes 50R of an implantable prosthesis is intersected by another through-hole.

The drug elution characteristics of a stent can be customized by selective positioning and distribution of any one or a combination of transverse, axial and radial through-holes. The positioning and distribution can run along one or both of the longitudinal length and the circumference of an implantable prosthesis. Greater uniformity of drug concentration emanating from the implantable prosthesis could be achieved by having non-radial through-holes. The phrase "non-radial through-holes" includes all through-holes which extend in a non-radial direction, for example, transverse through-holes, axial through-holes, and through-holes oriented at oblique angles to the central axis of the stent.

Figure 16:
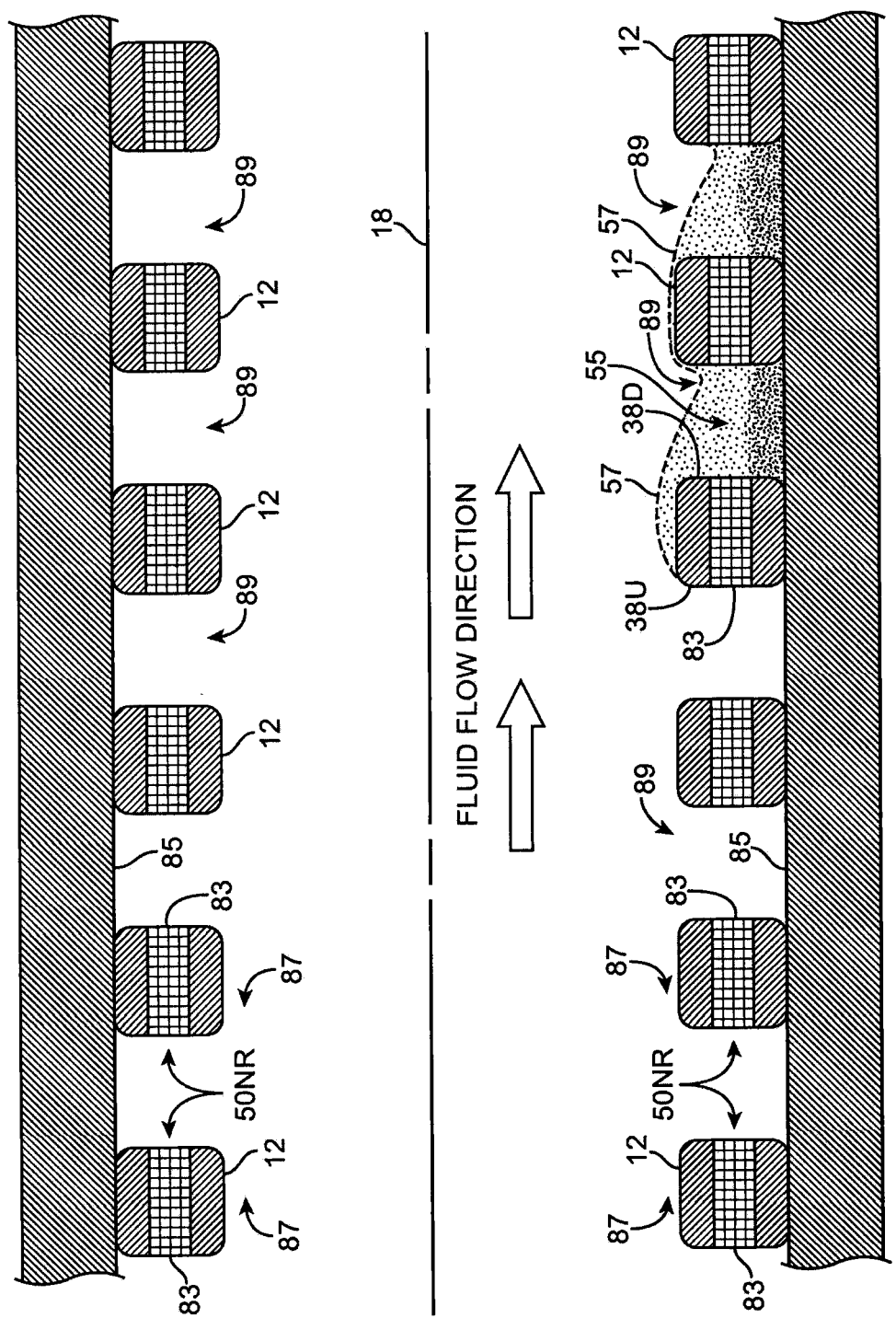
FIG. 16 is a longitudinal cross-sectional view of a stent that is deployed in an anatomical lumen, showing stent struts which do not release any drug directly out from through-holes to the lumen wall, and showing a boundary layer of fluid-solubilized drug being carried in a boundary layer to areas of the lumen wall between the stent struts.

Struts can have side surfaces 38U that face upstream (e.g., against the direction of blood flow in an artery) and side surfaces 38D that face downstream in the opposite direction (see FIG. 16). Quantities of the drug which elute or release from luminal surfaces and downstream-facing side surfaces 38D can form a drug-rich boundary layer 55 downstream of the strut, which has the effect of delivering the drug to the vessel wall far from the strut.

Considering that with most stents, the struts only occupy only 15-30% of the vessel wall area, a highly non-uniform drug distribution in the vessel wall might be anticipated. However, it has been shown that drug eluting stents create a drug rich boundary layer that flows along the vessel wall. This boundary layer serves to distribute the drug from the struts to the regions farthest from the struts, sometimes referred to as the middle of the stent pattern cells (V. B. Kolachalama, et al. J. of Controlled Release 133 (2009) 24-30.) It was assumed that to deliver drug to the vessel wall, drug must be released from the abluminal surface of the strut. However, this concept illustrates how drug released from the sidewall and luminal surface plays an important role in achieving uniform drug deposition into the vessel wall, without contributing to the high drug concentration hotspot that forms beneath the stent struts from the abluminal drug release.

In FIG. 16, the broken line 57 represents a boundary between fluid flowing in the anatomical lumen containing no drug from the stent and fluid flowing in the anatomical lumen having some drug released from the stent struts. Although the boundary layer 55 is partially illustrated only for two stent struts, it is to be understood that the boundary layer exists throughout the longitudinal length of the stent. Up to 43% of flow mediated deposition of drug into the vessel wall from blood-solubilized drug can come primarily from side surfaces. As such, it is believed that having more drug released from side surfaces (for example, released out of non-radial through-holes) can decrease drug concentration variability and increase concentration uniformity across the strut pattern over the entire length of the stent.

To facilitate flow mediated deposition and, thereby increase drug concentration uniformity, a greater number axial through-holes or transverse through-holes can be formed throughout or in selected segments of an implantable prosthesis. In some embodiments, an implantable prosthesis has no radial through-holes and has only axial through-holes and/or transverse through-holes.

In other embodiments, there is a gradient or variation in $N_{NON-RADIAL}/(N_{TOTAL})$, which is the ratio of, on one hand, the number of non-radial through-holes at a given position to, on the other hand, the total number of through-holes at the given position. An increase in the ratio value corresponds to an increase in the number of non-radial through-holes relative to the total number of through-holes.

Figure 10:
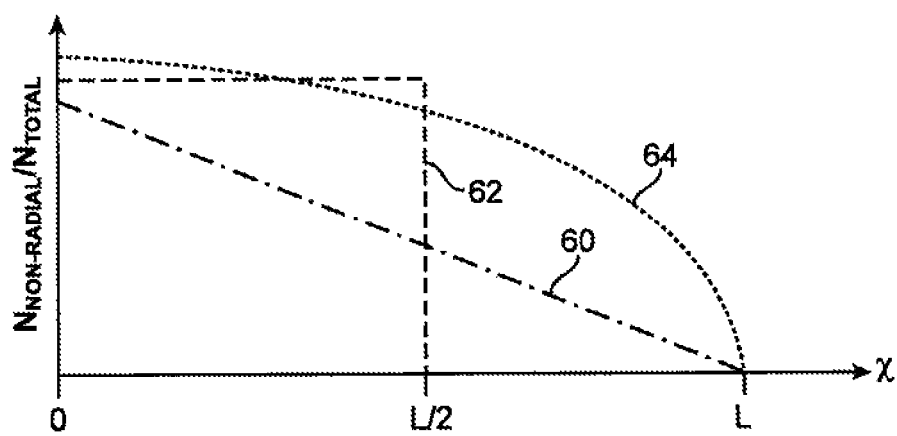
FIG. 10 is a graph of longitudinal position along the overall length of a stent versus the ratio of the number of non-radial through-holes to the total number of through-holes, showing three examples of a gradient in the ratio value versus longitudinal position.

The gradient can run across the overall length, L, of an implantable prosthesis, as shown in FIG. 10, where the horizontal axis indicates longitudinal position, x, on the implantable prosthesis and the vertical axes indicates the value of the ratio $N_{NON-RADIAL}/(N_{TOTAL})$. The longitudinal gradient can be a substantially linear gradient 60, a stepped gradient 62, or curved or non-linear gradient 64. These gradients 60, 62, 64 can slope or progress upwards or, as shown in FIG. 10, they can slope or progress downwards.

In FIG. 11, a longitudinal cross-section of a stent is shown as a non-limiting example of a stent having a longitudinal, stepped gradient corresponding to line 62 of FIG. 10. In other embodiments, the longitudinal gradient can be any multiple, series, or combination of increases and/or decreases that are linear, stepped, and/or curved.

Figure 12:
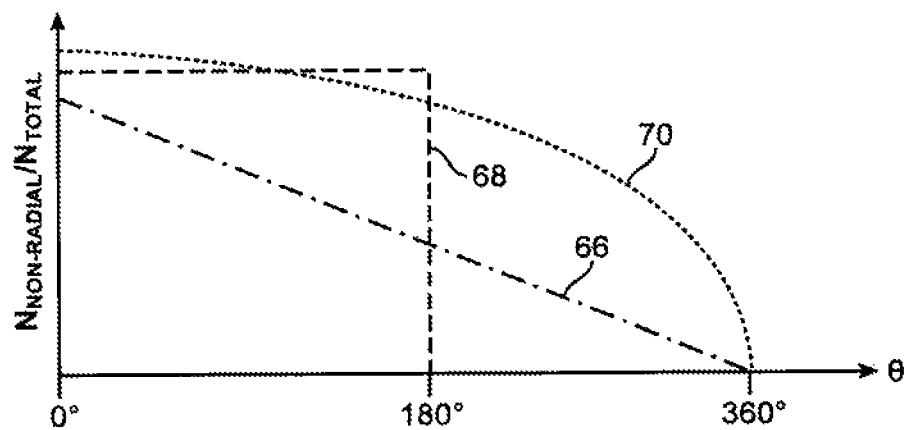
FIG. 12 is a graph of circumferential position around the circumference of a stent versus the ratio of the number of non-radial through-holes to the total number of through-holes, showing three examples of a gradient in the ratio value versus circumferential position.

The gradient can run around the circumference of an implantable prosthesis, as shown in FIG. 12, where the horizontal axis indicates circumferential position, θ, on the implantable prosthesis and the vertical axes indicates the value of the ratio $N_{NON-RADIAL}/(N_{TOTAL})$. The circumferential gradient can be a substantially linear gradient 66, a stepped gradient 68, or curved or non-linear gradient 70. These gradients 66, 66, 68 can slope or progress upwards or, as shown in FIG. 12, they can slope or progress downwards.

Figure 13:
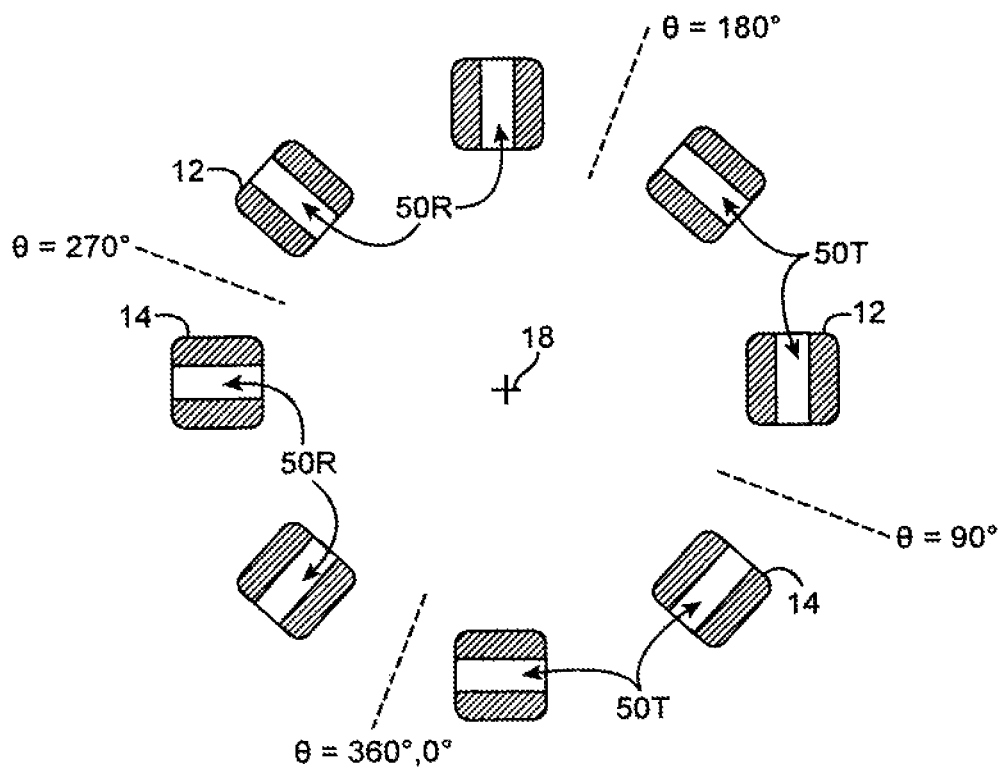
FIG. 13 is a radial cross-sectional view of a stent having a circumferential, stepped gradient in the ratio of the number of non-radial through-holes to the total number of through-holes.

In FIG. 13, a radial cross-section of a stent is shown as a non-limiting example of a stent having a circumferential, stepped gradient corresponding to line 68 of FIG. 12. In other embodiments, the circumferential gradient can be any multiple, series, or combination of increases and/or decreases that are linear, stepped, and/or curved.

In some embodiments, the gradient in the proportion of non-radial through-holes occurs longitudinally and circumferentially in the same implantable prosthesis.

Embodiments of the present invention include implantable prostheses having the through-holes described above in connection with FIGS. 4-13 and described below in connection with FIG. 15, wherein none, some, or all the through-holes are filled with a drug and/or drug-polymer composition. In the above and following description, the word "drug" in the singular includes the plural unless expressly stated otherwise. It is to be understood that the word "drug" includes one such drug, two such drugs, or under the right circumstances as determined by those skilled in the treatment of diseased tissues, even more such drugs unless it is expressly stated or is unambiguous from the context that such is not intended.

The drug and/or drug-polymer composition can be deposited inside through-holes in a number of ways. For example, an implantable prosthesis with through-holes can be immersed in, painted with, or sprayed with a liquid containing a desired drug. The liquid can be a solution of the drug and a biodegradable polymer dissolved in a solvent. The liquid can be a pure drug heated about its melting point. The liquid is allowed to pass into the through-holes and allowed to dry at room temperature or at an elevated temperature above room temperature. A composition of the drug and polymer remains after the solvent evaporates. The drug-polymer composition bonds or adheres to the walls of the through-holes. Excess amounts of the composition can be cleaned off all or some of the abluminal and/or luminal surfaces. Excess amounts of the composition can also be cleaned off all of the exterior surfaces (luminal, abluminal and side surfaces) of the implantable prosthesis so that the drug carried is carried exclusively in the through-holes.

Alternatively or in combination with the above methods, the drug can be deposited into the through-holes by a method in which discrete droplets of liquid are discharged such that each droplet travels in a controlled trajectory. A system and method for depositing droplets having a controlled trajectory onto a stent is described in U.S. Pat. No. 7,208,190 to Verlee et al, which is incorporated herein by reference. In some embodiments, the controlled trajectory intersects selected abluminal, luminal, and side surfaces. In other embodiments, a feedback camera or optical device is implemented to insure that the drug is deposited only on the side surfaces and in the through-holes, so that abluminal and luminal surfaces are free of any drug. In other embodiments, the feedback camera or optical device is implemented to insure that the drug is deposited only in the through-holes, so that the drug is carried exclusively in the through-holes. A method of controlling where a drug is deposited by means of a feedback camera or optical device is described in U.S. Pat. No. 6,395,326 to Castro et al., which is incorporated herein by reference.

The through-holes can be formed in the struts in a number of ways. In some-embodiments, a laser is used to vaporize or otherwise remove material from the struts. The laser is aimed at a predetermined surface of a particular strut of a stent. To form a non-radial through-hole, such as a transverse or axial through-hole, the laser is aimed toward a side surface of a strut. To form a radial through-hole, the laser is aimed toward a luminal or abluminal surface of a strut. A laser system and method for making a stent is described in U.S. Pat. No. 6,521,865 to Jones, et al., which is incorporated herein by reference.

After application of the laser, the resulting through-hole is bounded by the base material or substrate material of the stent strut. The phrase "substrate material" refers to the material at the core of the stent strut and does not include any coatings of other material added after initial formation of the core. The substrate material can be porous or, alternatively, substantially non-porous. In some embodiments, each through-hole is bounded by or formed into a porous substrate material. A porous substrate material can be the result of particles of metal or polymer that have been sintered or fused together such that small gaps or pores remain between the fused particles. The through-holes of the present invention are different from pores between sintered particles. Such pores are not located at predetermined positions on a stent strut as they are randomly distributed between particles. Also, such pores do not interconnect to form a channel or passageway in a particular direction. In many instances, such pores merely create surface roughness or sealed air pockets with no channel or pathway that extends entirely through a structure.

Particles and pores of a sintered stent substrate can have a mean diameter from submicron to tens of microns. In some embodiments, the through-holes formed into the stent substrate are several times larger in diameter than the pores. In some embodiments, the through-holes have a mean diameter that is from 2 to 200 times larger than the mean diameter of the pores, and more narrowly from 10 to 100 times larger than the mean diameter of the pores, and more narrowly from 10 to 50 times larger than the mean diameter of the pores.

Figure 14:
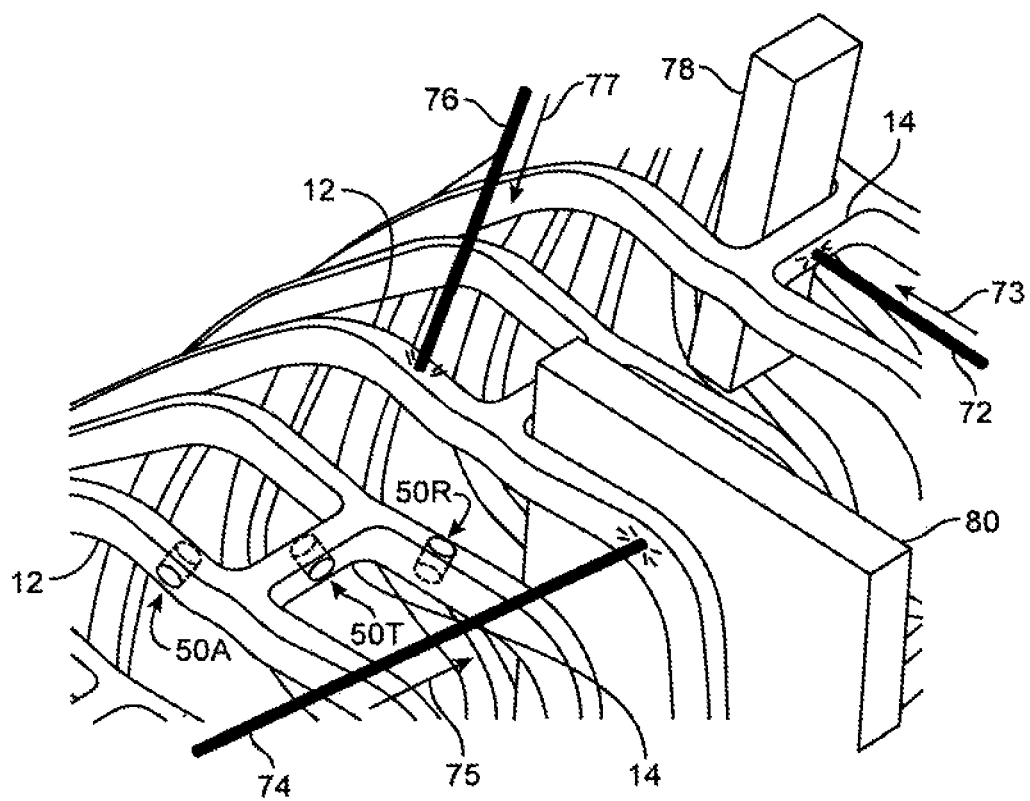
FIG. 14 is perspective view of a portion of a stent in an expanded state, showing laser beams making through-holes in the stent struts with shields protecting adjacent stent struts from the laser beams.

As shown in FIGS. 4 and 14, a laser beam 72 can be oriented in a transverse direction 73 relative to the central axis 18 of a stent to form a transverse through-hole. A shield 78, which can be in the form of a block of metal or ceramic, can be placed between the struts so that the laser beam forms a transverse through-hole in only a preselected strut and not in adjacent struts.

As shown in FIG. 14, a laser beam 74 can be oriented in a direction 75 that is at a slight angle, such as 5 degrees to 30 degrees, from the central axis of the stent to form an axial through-hole. Depending on the location of the strut, the laser beam can oriented at a direction that is substantially parallel to the stent central axis in order to form axial through-holes. A shield 80, which can be in the form of a metal plate, can be placed between the struts so that the laser beam forms an axial through-hole in only a preselected strut and not in adjacent struts.

As shown in FIGS. 7 and 14, a laser beam 76 can be oriented in a radial direction 77 relative to the central axis 18 of a stent to form radial through-holes. A shield 82, which can be in the form of a metal rod, can be placed in the central passageway of the stent so that the laser beam forms a radial through-hole in only a preselected strut and not in other struts.

Alternatively, or in combination with techniques described above and below, through-holes can be formed by etching the strut substrate material. The substrate material can be in the form of a sheet. Applied onto the sheet is a removable mask layer having a predetermined pattern of openings that corresponds to a desired pattern of non-radial through-holes. A chemical solution is applied so that unmasked areas of the sheet can be etched or eroded by the chemical to form one or more open channels or grooves in the sheet that corresponds to the desired pattern of non-radial through-holes. The sheet with grooves can be rolled up to form an inner layer of a tubular stent body. A second sheet of the substrate material can be used as an outer layer of the tubular stent body. After removal of the mask layer, the second sheet can be laminated, bonded or adhered over the rolled-up sheet so as to cover the grooves. A method for laminating layers of material to form a tubular prosthesis is described in U.S. Pat. No. 7,335,227 to Jalisi, which is incorporated by reference herein. A desired pattern of stent struts can be cut from the tube by a mechanical cutting tool or a laser. The resulting framework of interconnected struts will have non-radial through-holes. Alternatively, a pattern of stent struts can be cut from the flat sheet of the substrate material after the etching step but before the sheet is rolled. Also, a pattern of stent struts can be cut from a flat sheet of the substrate before the etching step.

Alternatively, or in combination with techniques described above and below, a direct rapid prototyping method can be employed to form a stent having the above-described through-holes. Rapid prototyping refers to methods of automatically constructing three dimensional objects from digital information derived from a computer-aided design file. The derived digital information can be in the form of an "STL" file, which is a file format used by stereolithography machines and the like. Rapid prototyping methods can make fully functional, production-quality objects in addition to prototypes. One rapid prototyping method involves depositing discrete or continuous amounts of a substrate material in multiple planar layers. The droplets adhere to each other so that each layer has a predetermined pattern of the substrate material. The layers are formed successively on top of each other to build a three-dimensional tubular frame of interconnected struts with through-holes. Rapid prototyping methods to form a stent according to the present invention also includes a Metal Printing Process (MPP), such as described in U.S. Patent Application Publication No. 2008/0057102 (U.S. application Ser. No. 11/839,104), which is incorporated herein by reference.

It is also contemplated that an electropolishing probe or an EMD (electrical discharge machining) electrode can be used form the through-holes as an alternative or in combination with the above laser and chemical etching methods. The probe or electrode can be applied to the substrate material to erode material away.

Any combination of the above described methods for forming through-holes may be employed in a single implantable prosthesis. For example, non-radial through-holes can be formed by etching and/or rapid prototyping, and radial-through-holes in the same stent can be formed by laser am/or electrical discharge machining.

Figure 15:
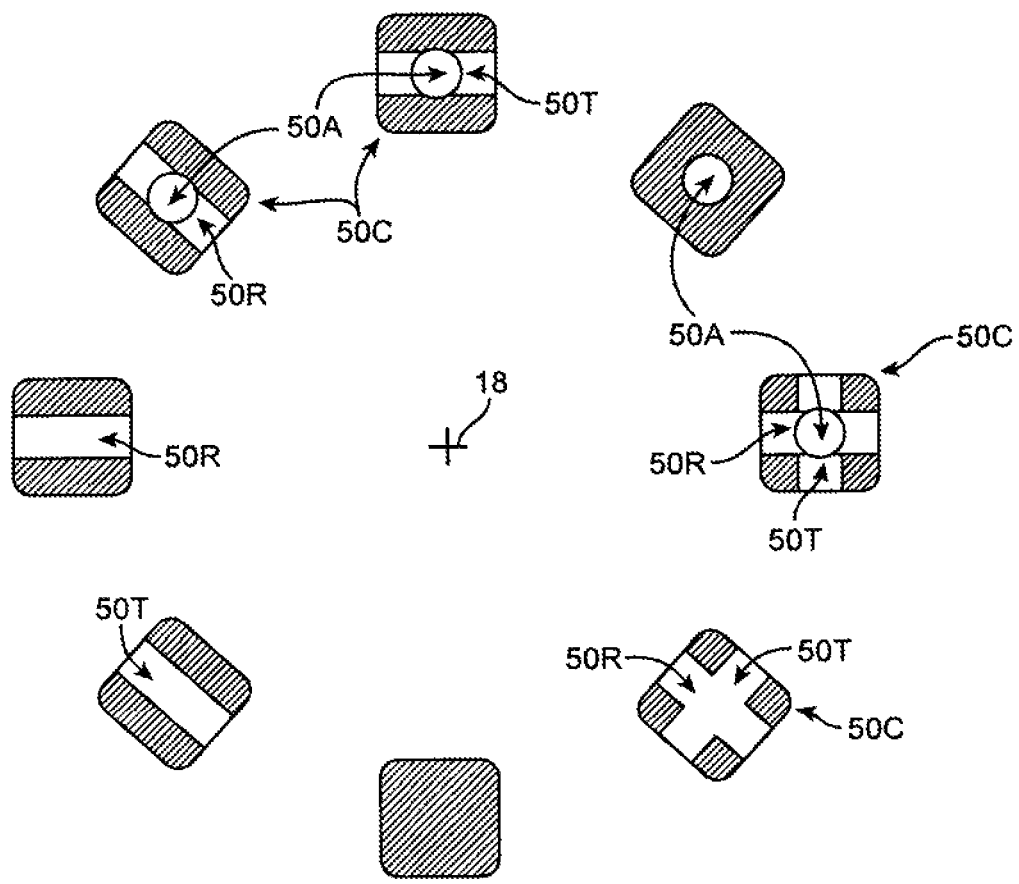
FIG. 15 is a radial cross-sectional view of a stent, showing a variety of through-hole types.

It will be appreciated that a stent can include any combination in the type of through-holes, such as shown in FIG. 15. In other embodiments, all the through-holes in an implantable prosthesis are oriented in the same way, either transversely, axially or radially. In some embodiments, all or some of the through-holes of an implantable prosthesis are oriented at one or more oblique angles from a central axis. The term "oblique angle" refers to a direction that is not perpendicular and not parallel to the central axis of an implantable prosthesis.

As shown in FIG. 16, in some embodiments none of the through-holes in stent struts are oriented radially. The stent only has non-radial through-holes 50NR, so that none of the drug 83 in the through-holes is released directly into the surrounding walls 85 of a vessel or anatomical lumen in which the stent is deployed. Applicant believes that this may increase drug concentration uniformity across the strut pattern by increasing flow mediated deposition of blood-solubilized drug to areas 89 of the vessel wall between the struts and reducing direct deposition of the drug at abluminal areas of contact with the vessel wall. Also, because there are no radial-through-holes, no drug is released directly from the through-hole opening to a luminal region 87 radially below the struts.

In FIG. 16, the drug 83 is in the form of a solid cylinder having a size and shape that corresponds to the size and shape of the non-radial through-holes 50NR. Each of the non-radial through-holes has a diameter that is substantially uniform throughout its entire end-to-end length. That is, the diameter of the through-hole and the solid cylinder (prior to degradation) is substantially the same through the entire end-to-end length. In some embodiments, the solid cylinder includes a biodegradable polymer impregnated with a therapeutic agent. The therapeutic agent is released into the flow of body fluid as the polymer is degraded by the body fluid flowing through the central passageway of the prosthesis.

Embodiments of the present invention include the above described configurations of through-holes, with or without a drug within the through-holes, in combination a coating layer containing a drug. In some embodiments, the coating layer is on all external surfaces, including abluminal, luminal and side surfaces. In other embodiments, none of the coating layer is on any of the abluminal and luminal surfaces, and the coating layer is on one or more side surfaces exclusively. In other embodiments, none of the coating layer is on any of the abluminal surfaces, and the coating layer is on one or more side and luminal surfaces. In other embodiments, none of the coating layer is on any of the luminal surfaces, and the coating layer is on one or more of the side and abluminal surfaces.

It will be appreciated that through-holes can be provided in a number of implantable prostheses, including without limitation self-expandable stents, balloon-expandable stents, grafts, and stent-grafts. An implantable prosthesis is a device that is totally or partly introduced, surgically or medically, into a patient's body. The duration of implantation may be essentially permanent, i.e., intended to remain in place for the remaining lifespan of the patient; until the device biodegrades; or until the device is physically removed. The prosthesis having through-holes of the present invention can be configured for intraluminal delivery of a drug and can be configured to be implanted by intraluminal methods, such as by a catheter delivery device known in the art, of by other implantation methods.

An implantable medical device specifically designed and intended solely for the localized delivery of a therapeutic agent is within the scope of this invention. At present, a preferred implantable medical device comprises a stent. The stent can have bare metal, uncoated struts having through-holes as described above, with a drug-polymer composition in the through-holes, the polymer being poly (D,L-lactide-co-glycolide), also referred to as PLGA. Other suitable polymers include without limitation poly(D,L-lactide), poly (L-lactide), poly(L-lactide-co-glycolide), poly(D,L-lactide-co-L-lactide), poly(carpolactone), poly(glycolide-co-caprolactone), poly(D,L-lactide-co-caprolactone), and poly(L-lactide-co-caprolactone). The bare metal struts have substantially smooth and non-porous external surfaces.

The substrate material of the prosthesis can be any suitable material known in the art of stents and other implantable devices. Substrate materials include without limitation nitinol or nickel-titanium alloys having shape memory and superelastic properties, other shape-memory metal alloys or polymers, stainless steel (such as 316L), nickel-cobalt-chromium-molybdenum alloys (such as MP35N), cobalt-chromium-tungsten-nickel-iron alloys (such as L605 or chonichrome), titanium, and tantalum.

The drug carried within and/or on the prosthesis substrate material can be any suitable therapeutic agent known in the art of stents and other implantable devices. The therapeutic agent can be in a substantially pure form. The therapeutic agent can be mixed, dispersed, dissolved, encapsulated or otherwise carried in a polymer.

Therapeutic agents include without limitation an anti-restenosis agent, an antiproliferative agent, an anti-inflammatory agent, an antineoplastic, an antimitotic, an antiplatelet, an anticoagulant, an antifibrin, an antithrombin, a cytostatic agent, an antibiotic, an anti-enzymatic agent, an angiogenic agent, a cyto-protective agent, a cardioprotective agent, a proliferative agent, an ABC A1 agonist, an antioxidant, a cholesterol-lowering agent, aspirin, an angiotensin-converting enzyme, a beta blocker, a calcium channel blocker, nitroglycerin, a long-acting nitrate, a glycoprotein IIb-IIIa inhibitor or any combination thereof.

Examples of antiproliferative agents include, without limitation, actinomycins, taxol, docetaxel, paclitaxel, rapamycin, 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin, zotarolimus, ABT-578, everolimus, biolimus, novolimus, myolimus, deforolimus, temsirolimus, perfenidone and derivatives, analogs, prodrugs, co-drugs and combinations of any of the foregoing.

Examples of anti-inflammatory agents include, without limitation, both steroidal and non-steroidal (NSAID) anti-inflammatory agents such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclofenac, ciclofenin, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecrolimus and derivatives, analogs, prodrugs, co-drugs and combinations of any of the foregoing.

Examples of antineoplastics and antimitotics include, without limitation, paclitaxel, docetaxel, methotrexate, azathioprine, vincristine, vinblastine, fluorouracil, doxorubicin hydrochloride, and mitomycin.

Examples of antiplatelet, anticoagulant, antifibrin, and antithrombin drugs include, without limitation, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as Angiomax a, calcium channel blockers such as nifedipine, colchicine, fish oil (omega 3-fatty acid), histamine antagonists, lovastatin, monoclonal antibodies such as those specific for Platelet-Derived Growth Factor (PDGF) receptors, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic, 4-amino-2,2,6, 6-tetramethylpiperidine-1-oxyl (4-amino-TEMPO) and derivatives, analogs, prodrugs, codrugs and combinations thereof.

Examples of cytostatic agents include, without limitation, angiopeptin, angiotensin converting enzyme inhibitors such as captopril, cilazapril or lisinopril, calcium channel blockers such as nifedipine; colchicine, fibroblast growth factor (FGF) antagonists, fish oil (ω-3-fatty acid), histamine antagonists, lovastatin, monoclonal antibodies such as, without limitation, those specific for Platelet-Derived Growth Factor (PDGF) receptors, nitroprusside, phosphodiesterase inhibitors, prostaglandin inhibitors, suramin, serotonin blockers, steroids, thioprotease inhibitors, triazolopyrimidine (a PDGF antagonist) and nitric oxide.

As indicated above, the therapeutic agent can be carried in a polymer matrix or composition, and the therapeutic agent can be carried in a polymer coating applied to one or more external surfaces of the prosthesis. The agent-polymer composition in the through-holes can be different from that on the external surface coating. The respective agent-polymer compositions can contain the same agent but can differ in terms of rate of bioabsorption of the polymer and/or rate or release of the agent. The respective agent-polymer compositions can contain a different agent in the through-holes than on the external surfaces, the difference being in agent concentration, chemical structure, or both. The term "agent concentration" refers to the amount of agent per volume of agent-polymer composition.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. An implantable prosthesis comprising:
   a tubular frame of interconnected structural members, the structural members having non-intersecting through-holes that are straight with no bend, each of the through-holes having a first end opening, a second end opening, and an interior wall, the first end opening and the second end opening formed through external surfaces of the tubular frame, the interior wall connecting the first end opening to the second end opening, some of the through-holes belong to a first plurality of the through-holes and each have a length that extends in a non-radial direction from the first end opening to the second end opening, and some of the through-holes belong to a second plurality of the through-holes and each have a length that extends in a radial direction from the first end opening to the second end opening; and
   a therapeutic agent within the through-holes,
   wherein at each of a plurality of axial positions on the tubular frame, there is a ratio of through-holes belonging to the second plurality of through-holes relative to a total number of the through-holes at the axial position, and the ratio increases along an axial direction parallel to a central axis of the tubular frame.

2. The prosthesis of claim 1, further comprising a polymer within the through-holes, the polymer combined with the therapeutic agent.

3. The prosthesis of claim 1, wherein the polymer is bioabsorbable.

4. The prosthesis of claim 1, wherein the structural members form a plurality of rings and a plurality of links, each ring configured for radial expansion, the rings connected to each other by the links.

5. The prosthesis of claim 1, wherein the non-radial direction of at least some of the through-holes of the first plurality of through-holes is substantially parallel to a central axis of the tubular frame.

6. The prosthesis of claim 1, wherein the non-radial direction of at least some of the through-holes of the first plurality of through-holes is substantially perpendicular to a central axis of the tubular frame.

7. The prosthesis of claim 1, wherein the through-holes are formed in a substantially non-porous material.

8. The prosthesis of claim 1, further comprising a coating on an external surface of the structural members, the coating including a therapeutic agent that is the same as or different from the therapeutic agent within the through-holes.

9. The prosthesis of claim 8, wherein no therapeutic agent is disposed over any radially inward facing surface of the tubular frame, and no therapeutic agent is disposed over any radially outward facing surface of the tubular frame.

10. The prosthesis of claim 1, wherein the structural members, which have the through-holes belonging to the first plurality of through-holes, have no radial though-hole.

11. The prosthesis of claim 1, wherein no therapeutic agent is located at any radially inward facing part and any radially outward facing part of the structural members having the through-holes belonging to the first plurality of through-holes.

12. The prosthesis of claim 1, wherein the structural members are flexible and the tubular framework is configured to radially expand.

13. The prosthesis of claim 1, wherein the non-radial direction is substantially parallel to a central axis of the tubular frame or is tangent to an imaginary circle around the central axis of the tubular frame.

14. The prosthesis of claim 1, wherein the increase in the ratio continues from a first end of the tubular frame to a second end of the tubular frame.

15. The prosthesis of claim 14, wherein the non-radial direction of each of the through-holes belonging to the second plurality of through-holes, is substantially parallel to the central axis of the tubular frame or is tangent to an imaginary circle around the central axis of the tubular frame.

16. The prosthesis of claim 14, wherein the ratio is lowest at the second end of the tubular frame.

17. The prosthesis of claim 16, wherein the ratio is highest at the first end of the tubular frame.

18. An implantable prosthesis comprising:
a tubular frame of interconnected structural members, the structural members having non-intersecting through-holes that are straight with no bend, each of the through-holes having a first end opening, a second end opening, and an interior wall, the first end opening and the second end opening formed through external surfaces of the tubular frame, the interior wall connecting the first end opening to the second end opening, some of the through-holes belong to a first plurality of the through-holes and each have a length that extends in a non-radial direction from the first end opening to the second end opening, and some of the through-holes belong to a second plurality of the through-holes and each have a length that extends in a radial direction from the first end opening to the second end opening; and
a therapeutic agent within the through-holes,
wherein at each of a plurality of circumferential positions on the tubular frame, there is a ratio of through-holes belonging to the second plurality of through-holes relative to a total number of the through-holes at the circumferential position, and the ratio increases along a circumferential direction around a central axis of the tubular frame.

* * * * *